United States Patent
Bai et al.

(10) Patent No.: US 10,242,923 B2
(45) Date of Patent: Mar. 26, 2019

(54) FORMULATIONS CONTAINING MIXED RESIN SYSTEMS AND THE USE THEREOF FOR WAFER-LEVEL UNDERFILL FOR 3D TSV PACKAGES

(71) Applicants: HENKEL IP & HOLDING GMBH, Duesseldorf (DE); HENKEL AG & CO. KGAA, Duesseldorf (DE)

(72) Inventors: Jie Bai, Aliso Viejo, CA (US); Qiaohong Huang, Trabuco Canyon, CA (US); Hong Jiang, Irvine, CA (US); Youko Murata, Kanagawa (JP); Yusuke Horiguchi, Kanagawa (JP); YounSang Kim, Foothill Ranch, CA (US); Tadashi Takano, Yokohama (JP)

(73) Assignees: HENKEL IP & HOLDING GMBH, Duesseldorf (DE); HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 15/945,772

(22) Filed: Apr. 5, 2018

(65) Prior Publication Data
US 2018/0226313 A1    Aug. 9, 2018

Related U.S. Application Data

(63) Continuation of application No. PCT/US2016/055698, filed on Oct. 6, 2016.
(Continued)

(51) Int. Cl.
*H01L 23/48*    (2006.01)
*H01L 23/52*    (2006.01)
(Continued)

(52) U.S. Cl.
CPC .......... *H01L 23/293* (2013.01); *C08F 283/10* (2013.01); *C08G 59/18* (2013.01);
(Continued)

(58) Field of Classification Search
CPC ....... H01L 2924/181; H01L 2924/0665; H01L 2224/45099; H01L 3334/29099;
(Continued)

(56) References Cited

U.S. PATENT DOCUMENTS

| 5,717,034 A | 2/1998 | Dershem et al. |
| 5,718,941 A | 2/1998 | Dershem et al. |

(Continued)

FOREIGN PATENT DOCUMENTS

JP    2008297373 A    12/2008

OTHER PUBLICATIONS

Rogers-Evans, M. et al., "Oxetanes as Versatile Elements in Drug Discovery and Synthesis." in Angew. Chem. Int. Ed. 2010, 49, pp. 9052-9067.

*Primary Examiner* — S. V. Clark
(74) *Attorney, Agent, or Firm* — Taylor M. Coon (57) ABSTRACT

Provided herein are mixed resin systems and the use thereof for wafer-level underfill (WAUF) for three-dimensional TSV packages. In one aspect, there are provided compositions comprising (1) an epoxy resin, (2) a maleimide, nadimide or itaconamide, (3) an acrylate and (4) a filler. In certain aspects, the epoxy resin is a siloxane-modified resin. In certain aspects, the invention relates to underfill films prepared from invention compositions. In certain aspects, the invention relates to articles comprising the underfill films described herein.

21 Claims, 4 Drawing Sheets

Related U.S. Application Data (60) Provisional application No. 62/238,184, filed on Oct. 7, 2015.

(51) Int. Cl.
*H01L 29/40* (2006.01)
*H01L 23/29* (2006.01)
*C08G 59/18* (2006.01)
*C08K 5/09* (2006.01)
*C08L 33/04* (2006.01)
*C08L 63/00* (2006.01)
*C09D 4/06* (2006.01)
*C08F 283/10* (2006.01)
*H01L 21/56* (2006.01)
*C09D 163/00* (2006.01)
*C08K 3/36* (2006.01)
*C08L 33/06* (2006.01)
*C08L 79/08* (2006.01)
*C08L 33/08* (2006.01)
*C08L 39/04* (2006.01)
*G01N 25/48* (2006.01)

(52) U.S. Cl.
CPC ............ *C08K 3/36* (2013.01); *C08K 5/09* (2013.01); *C08L 33/04* (2013.01); *C08L 33/06* (2013.01); *C08L 33/08* (2013.01); *C08L 39/04* (2013.01); *C08L 63/00* (2013.01); *C08L 79/085* (2013.01); *C09D 4/06* (2013.01); *C09D 163/00* (2013.01); *H01L 21/563* (2013.01); *C08L 2203/20* (2013.01); *G01N 25/4866* (2013.01)

(58) Field of Classification Search
CPC ......... H01L 21/563; H01L 2224/83855; H01L 2224/29298
USPC ....... 257/762, 782, 783, 787, 788, 789, 793; 438/118, 127
See application file for complete search history.

(56) References Cited

U.S. PATENT DOCUMENTS

| | | | |
|---|---|---|---|
| 6,833,629 B2 | 12/2004 | Ma et al. | |
| 2003/0170450 A1* | 9/2003 | Stewart | H05K 3/305 428/343 |
| 2010/0007018 A1 | 1/2010 | Wyatt et al. | |
| 2010/0178501 A1* | 7/2010 | Masuko | C09J 4/06 428/355 N |
| 2011/0151195 A1* | 6/2011 | Mitsukura | C08G 73/1042 428/156 |
| 2012/0133061 A1* | 5/2012 | Mitsukura | C08G 73/1039 257/798 |
| 2012/0156502 A1* | 6/2012 | Maejima | H01L 24/29 428/414 |
| 2016/0160102 A1* | 6/2016 | Minegishi | G03F 7/038 257/783 |

* cited by examiner

FORMULATIONS CONTAINING MIXED RESIN SYSTEMS AND THE USE THEREOF FOR WAFER-LEVEL UNDERFILL FOR 3D TSV PACKAGES

FIELD OF THE INVENTION

The present invention relates to mixed resin systems and methods for the use thereof for the preparation of wafer-level underfill (WAUF) for three-dimensional through-silica via (TSV) packages. In one aspect, the invention relates to compositions comprising a combination of at least (1) an epoxy resin, (2) a maleimide, nadimide or itaconamide, (3) an acrylate and (4) a filler. In certain aspects, the epoxy resin is a siloxane-modified resin. In certain aspects, the invention relates to underfill films prepared from invention compositions. In certain aspects, the invention relates to articles comprising the underfill films described herein. In certain embodiments, the invention relates to assemblies comprising a first article permanently adhered to a second article by a cured aliquot of a formulation as described herein.

SUMMARY OF THE INVENTION

In accordance with the present invention, there are provided mixed resin systems and methods for the use thereof for the preparation of wafer-level underfill (WAUF) for three-dimensional through-silica via (TSV) packages.

In one aspect, there are provided compositions comprising a combination of at least (1) an epoxy resin, (2) a maleimide, nadimide or itaconamide, (3) an acrylate and (4) a filler. In certain aspects, the epoxy resin is a siloxane-modified resin.

In certain aspects, there are provided underfill films prepared from invention compositions.

In certain aspects, there are provided articles comprising the underfill films described herein.

In certain aspects, there are provided assemblies comprising a first article permanently adhered to a second article by a cured aliquot of a formulation as described herein.

DETAILED DESCRIPTION OF THE INVENTION

Figure 1:
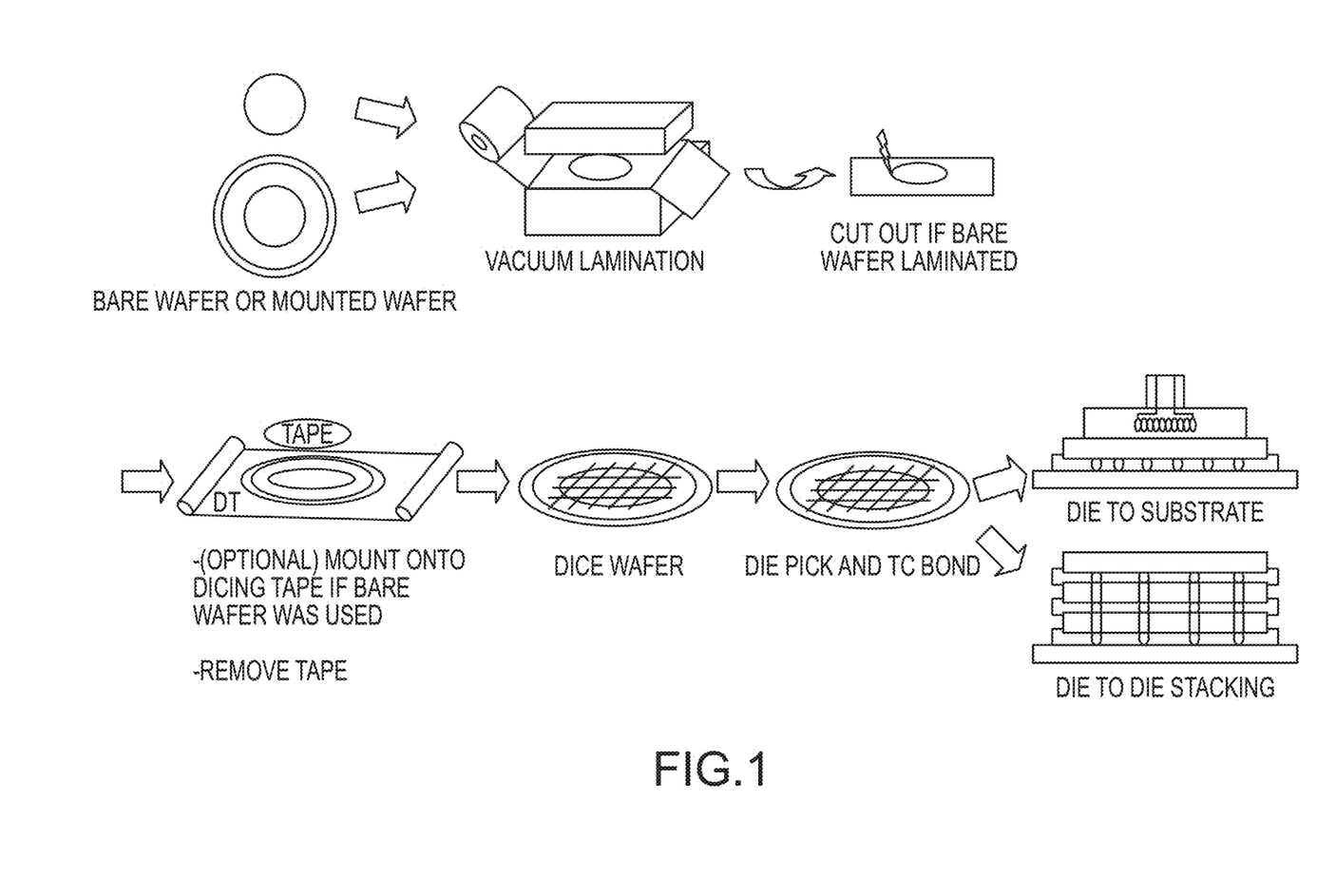
FIG. 1 presents a flow chart of exemplary steps employed to apply wafer level underfill (WAUF) employing formulations according to the present invention.
Figure 2:
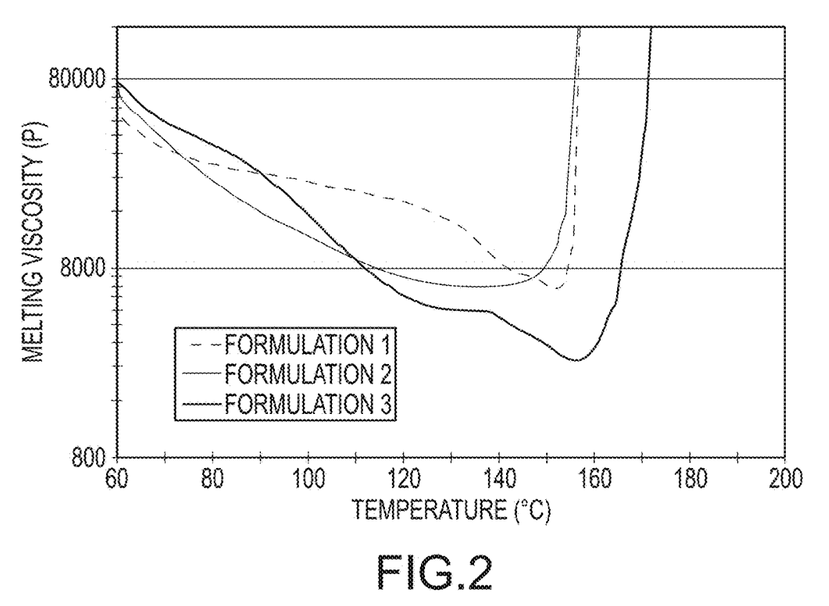
FIG. 2 presents melt viscosity data for various formulations. Once the scanning temperature reaches the onset gelling temperature of the subject material, the melt viscosity thereof significantly increases within a 5° C. temperature range and the material becomes a gel.
Figure 3:
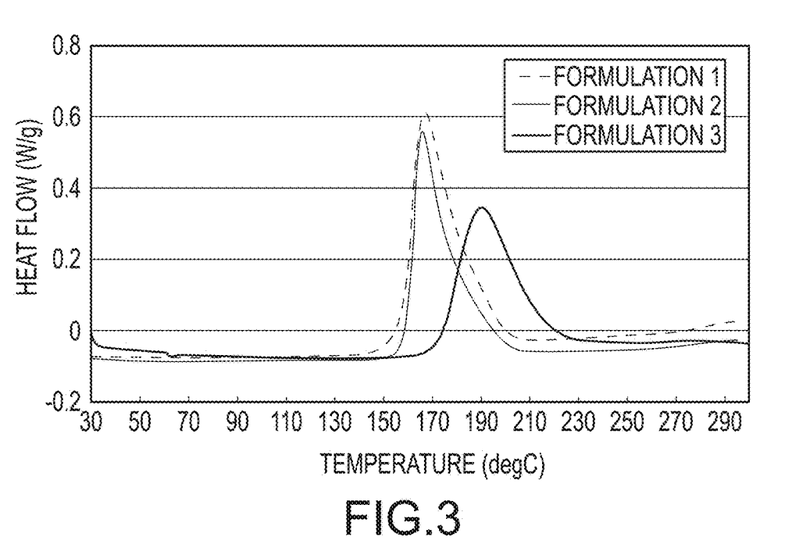
FIG. 3 presents differential scanning calorimetry (DCS) data for several formulations. All formulations show a sharp DSC onset, and the deltaT between "DSC onset" and "DSC peak" temperatures is less than 15° C.
Figure 4:
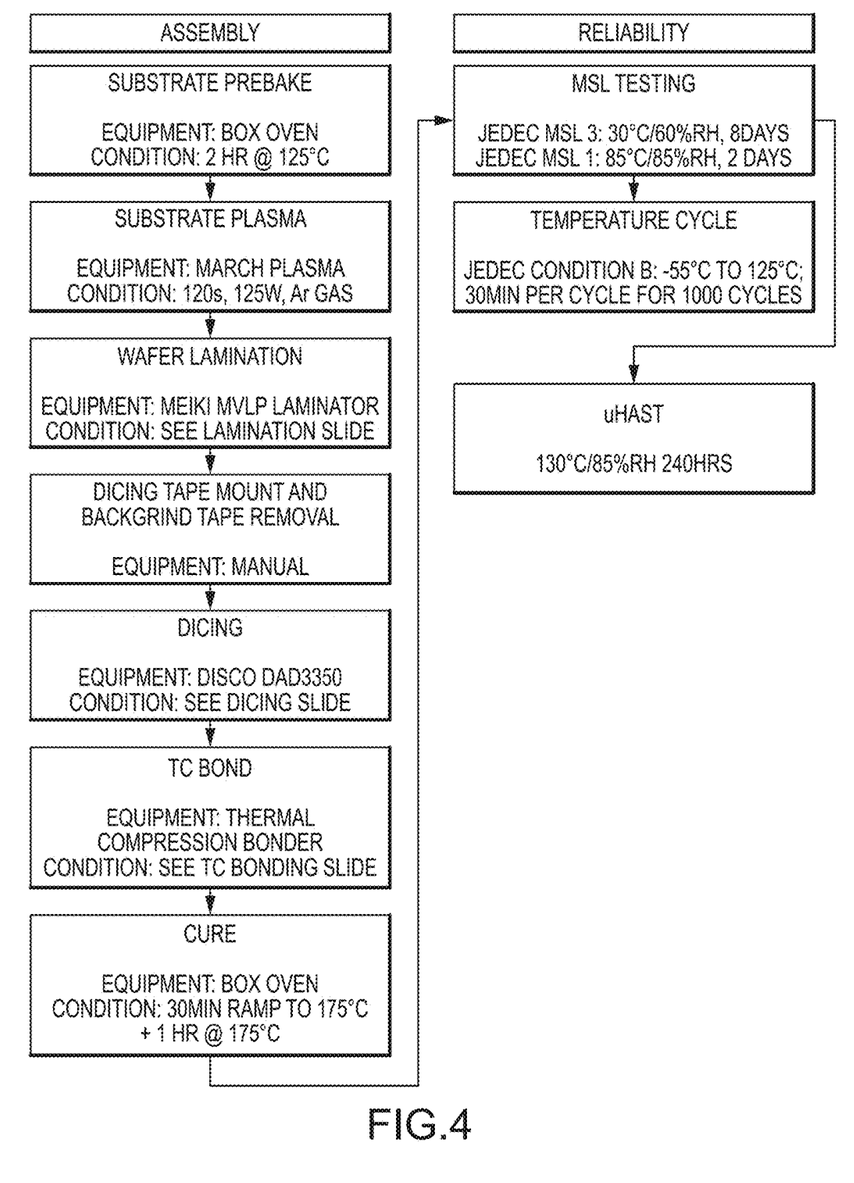
FIG. 4 presents an exemplary process flow for the assembly and reliability testing of films prepared employing formulations according to the present invention.
Figure 5:
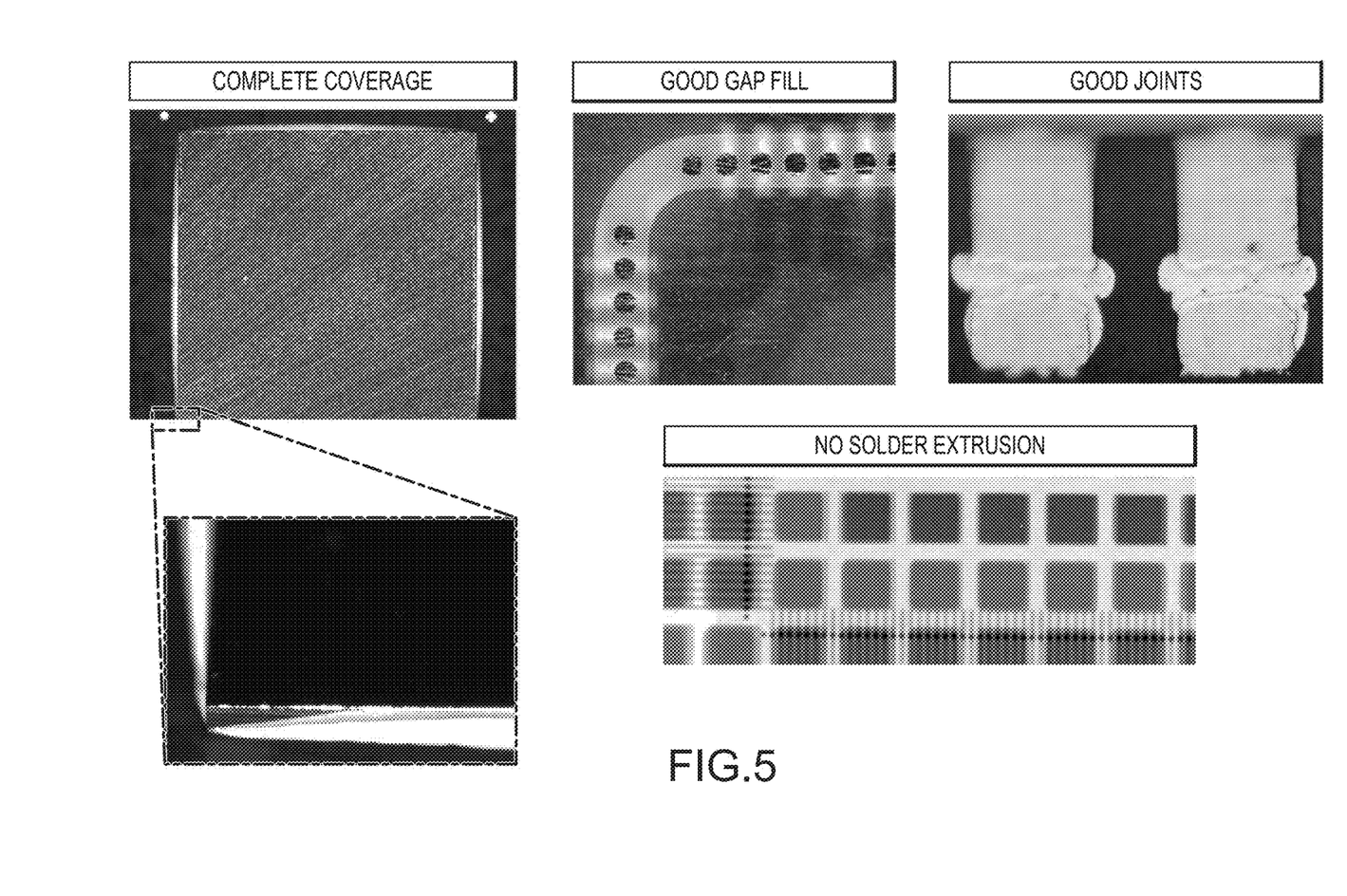
FIG. 5 presents the application testing results of formulations according to the present invention. Underfill film materials show good die corner coverage, gap filling, and electrical interconnect joint formation.

In accordance with the present invention, there are provided compositions comprising:

an epoxy resin;
a maleimide, nadimide or itaconimide;
an acrylate; and
a filler;
wherein:
said epoxy resin is a thermosetting resin which can cure into a three-dimensional polymer network;
said maleimide, nadimide or itaconimide is monomeric or oligomeric and can undergo radical cure to form a polymeric network;
said acrylate is monomeric or oligomeric and can undergo radical cure to form a polymeric network; and
said filler modulates the coefficient of thermal expansion (CTE) of the resulting composition;
wherein:
said composition, when cured, has a:
DSC onset of 100° C.-205° C.;
Melt viscosity in the range of 200 Poise-40,000 Poise, and
gelling temperature of 130° C.-180° C., as measured by Ares Rheometer at 10 Rad frequency with a 10° C./min ramp rate using a sample 1 inch in diameter and 1 mm thick.

In some embodiments, DSC onset falls in the range of 120° C.-205° C.; in some embodiments, DSC onset falls in the range of 140° C.-205° C.; in some embodiments, DSC onset falls in the range of 160° C.-205° C.; in some embodiments, DSC onset falls in the range of 180° C.-205° C.

In some embodiments, the melt viscosity falls in the range of 200 Poise-20,000 Poise; in some embodiments, the melt viscosity falls in the range of 200 Poise-10,000 Poise; in some embodiments, the melt viscosity falls in the range of 200 Poise-5,000 Poise; in some embodiments, the melt viscosity falls in the range of 200 Poise-1,000 Poise.

In some embodiments, the gelling temperature falls in the range of 140° C.-180° C., as measured by Ares Rheometer at 10 Rad frequency with a 10° C./min ramp rate using a sample 1 inch in diameter and 1 mm thick. In some embodiments, the gelling temperature falls in the range of 140° C.-170° C., in some embodiments, the gelling temperature falls in the range of 150° C.-180° C., in some embodiments, the gelling temperature falls in the range of 150° C.-170° C.

The thermosetting resin compositions of the present invention, as noted above, include among other constituents an epoxy component. A wide variety of epoxy-functionalized resins are contemplated for use herein, e.g., liquid-type epoxy resins based on bisphenol A, solid-type epoxy resins based on bisphenol A, liquid-type epoxy resins based on bisphenol F (e.g., Epiclon EXA-835LV), multifunctional epoxy resins based on phenol-novolac resin, dicyclopentadiene-type epoxy resins (e.g., Epiclon HP-7200L), naphthalene-type epoxy resins, and the like, as well as mixtures of any two or more thereof.

Exemplary epoxy-functionalized resins contemplated for use herein include the diepoxide of the cycloaliphatic alcohol, hydrogenated bisphenol A (commercially available as Epalloy 5000), a difunctional cycloaliphatic glycidyl ester of hexahydrophthallic anhydride (commercially available as Epalloy 5200), Epiclon EXA-835LV, Epiclon HP-7200L, and the like, as well as mixtures of any two or more thereof.

In certain embodiments, the epoxy component may include the combination of two or more different bisphenol based epoxies. These bisphenol based epoxies may be selected from bisphenol A, bisphenol F, or bisphenol S epoxies, or combinations thereof. In addition, two or more different bisphenol epoxies within the same type of resin (such A, F or S) may be used.

Commercially available examples of the bisphenol epoxies contemplated for use herein include bisphenol-F-type epoxies (such as RE-404-S from Nippon Kayaku, Japan, and EPICLON 830 (RE1801), 830S (RE1815), 830A (RE1826) and 830W from Dai Nippon Ink & Chemicals, Inc., and RSL 1738 and YL-983U from Resolution) and bisphenol-A-type epoxies (such as YL-979 and 980 from Resolution).

The bisphenol epoxies available commercially from Dai Nippon and noted above are promoted as liquid undiluted epichlorohydrin-bisphenol F epoxies having much lower viscosities than conventional epoxies based on bisphenol A epoxies and have physical properties similar to liquid bisphenol A epoxies. Bisphenol F epoxy has lower viscosity than bisphenol A epoxies, all else being the same between the two types of epoxies, which affords a lower viscosity and thus a fast flow underfill sealant material. The EEW of these four bisphenol F epoxies is between 165 and 180. The viscosity at 25° C. is between 3,000 and 4,500 cps (except for RE1801 whose upper viscosity limit is 4,000 cps). The hydrolyzable chloride content is reported as 200 ppm for RE1815 and 830W, and that for RE1826 as 100 ppm.

The bisphenol epoxies available commercially from Resolution and noted above are promoted as low chloride containing liquid epoxies. The bisphenol A epoxies have a EEW (g/eq) of between 180 and 195 and a viscosity at 25° C. of between 100 and 250 cps. The total chloride content for YL-979 is reported as between 500 and 700 ppm, and that for YL-980 as between 100 and 300 ppm. The bisphenol F epoxies have a EEW (g/eq) of between 165 and 180 and a viscosity at 25° C. of between 30 and 60. The total chloride content for RSL-1738 is reported as between 500 and 700 ppm, and that for YL-983U as between 150 and 350 ppm.

In addition to the bisphenol epoxies, other epoxy compounds are contemplated for use as the epoxy component of invention formulations. For instance, cycloaliphatic epoxies, such as 3,4-epoxycyclohexylmethyl-3,4-epoxycyclohexylcarbonate, can be used. Also monofunctional, difunctional or multifunctional reactive diluents may be used to adjust the viscosity and/or lower the Tg of the resulting resin material. Exemplary reactive diluents include butyl glycidyl ether, cresyl glycidyl ether, polyethylene glycol glycidyl ether, polypropylene glycol glycidyl ether, and the like.

Epoxies suitable for use herein include polyglycidyl derivatives of phenolic compounds, such as those available commercially under the tradename EPON, such as EPON 828, EPON 1001, EPON 1009, and EPON 1031 from Resolution; DER 331, DER 332, DER 334, and DER 542 from Dow Chemical Co.; and BREN-S from Nippon Kayaku. Other suitable epoxies include polyepoxides prepared from polyols and the like and polyglycidyl derivatives of phenol-formaldehyde novolacs, the latter of such as DEN 431, DEN 438, and DEN 439 from Dow Chemical. Cresol analogs are also available commercially under the tradename ARALDITE, such as ARALDITE ECN 1235, ARALDITE ECN 1273, and ARALDITE ECN 1299 from Ciba Specialty Chemicals Corporation. SU-8 is a bisphenol-A-type epoxy novolac available from Resolution. Polyglycidyl adducts of amines, aminoalcohols and polycarboxylic acids are also useful in this invention, commercially available resins of which include GLYAMINE 135, GLYAMINE 125, and GLYAMINE 115 from F.I.C. Corporation; ARALDITE MY-720, ARALDITE 0500, and ARALDITE 0510 from Ciba Specialty Chemicals and PGA-X and PGA-C from the Sherwin-Williams Co.

Appropriate monofunctional epoxy coreactant diluents for optional use herein include those that have a viscosity which is lower than that of the epoxy component, ordinarily, less than about 250 cps.

The monofunctional epoxy coreactant diluents should have an epoxy group with an alkyl group of about 6 to about 28 carbon atoms, examples of which include $C_{6-28}$ alkyl glycidyl ethers, $C_{6-28}$ fatty acid glycidyl esters, $C_{6-28}$ alkylphenol glycidyl ethers, and the like.

In the event such a monofunctional epoxy coreactant diluent is included, such coreactant diluent should be employed in an amount from about 0.5 percent by weight to about 10 percent by weight, based on the total weight of the composition; in some embodiments, such coreactant diluent should be employed in an amount from about 0.25 percent by weight to about 5 percent by weight, based on the total weight of the composition.

The epoxy component should be present in the composition in an amount in the range of about 1 percent by weight to about 20 percent by weight; in some embodiments, invention formulations comprise about 2 percent by weight to about 18 percent by weight epoxy; in some embodiments, invention formulations comprise about 5 to about 15 percent by weight epoxy.

In some embodiments, the epoxy component employed herein is a silane modified epoxy, e.g., a composition of matter that includes:
(A) an epoxy component embraced by the following structure:

where:
Y may or may not be present and when Y present is a direct bond, $CH_2$, $CH(CH_3)_2$, $C=O$, or S,
$R_1$ here is alkyl, alkenyl, hydroxy, carboxy and halogen, and
x here is 14;
(B) an epoxy-functionalized alkoxy silane embraced by the following structure:

$R^1$—$Si(OR^2)_3$ wherein
$R^1$ is an oxirane-containing moiety and
$R^2$ is an alkyl or alkoxy-substituted alkyl, aryl, or aralkyl group having from one to ten carbon atoms; and
(C) reaction products of components (A) and (B).

An example of one such silane-modified epoxy is formed as the reaction product of an aromatic epoxy, such as a bisphenol A, E, F or S epoxy or biphenyl epoxy, and epoxy silane where the epoxy silane is embraced by the following structure:

$R^1$—$Si(OR^2)_3$ wherein
$R^1$ is an oxirane-containing moiety, examples of which include 2-(ethoxymethyl)oxirane, 2-(propoxymethyl) oxirane, 2-(methoxymethyl)oxirane, and 2-(3-methoxypropyl)oxirane and
$R^2$ is an alkyl or alkoxy-substituted alkyl, aryl, or aralkyl group having from one to ten carbon atoms.
In one embodiment, $R^1$ is 2-(ethoxymethyl)oxirane and $R^2$ is methyl.

Idealized structures of the aromatic epoxy used to prepare the silane modified epoxy include wherein
Y may or may not be present, and when Y is present, it is a direct bond, CH$_2$, CH(CH$_3$)$_2$, C=O, or S,
R$_1$ is alkyl, alkenyl, hydroxy, carboxy or halogen, and x is 1-4.

Of course, when x is 2-4, chain extended versions of the aromatic epoxy are also contemplated as being embraced by this structure.

For instance, a chain extended version of the aromatic epoxy may be embraced by the structure below In some embodiments, the siloxane modified epoxy resin has the structure:

wherein:
Z is —O—(CH$_2$)$_3$—O-Ph-CH$_2$-Ph-O—(CH$_2$—CH(OH)—CH$_2$—O-Ph-CH$_2$-Ph-O—)$_n$—CH$_2$-oxirane, and
n falls in the range of about 1-4.

In some embodiments, the siloxane modified epoxy resin is produced by contacting a combination of the following components under conditions suitable to promote the reaction thereof:

+

+ wherein "n" falls in the range of about 1-4.

The silane modified epoxy may also be a combination of the aromatic epoxy, the epoxy silane, and reaction products of the aromatic epoxy and the epoxy silane. The reaction products may be prepared from the aromatic epoxy and epoxy silane in a weight ratio of 1:100 to 100:1, such as a weight ratio of 1:10 to 10:1.

Quantities of epoxy monomer(s) contemplated for use in invention compositions are sufficient so that the resulting formulation comprises in the range of about 1-20 wt % of said epoxy. In certain embodiments, the resulting formulation comprises in the range of about 2-18 wt % of said epoxy. In certain embodiments, the resulting formulation comprises in the range of about 5-15 wt % of said epoxy.

Epoxy cure agents are optionally employed in combination with epoxy monomer(s). Exemplary epoxy cure agents include ureas, aliphatic and aromatic amines, amine hardeners, polyamides, imidazoles, dicyandiamides, hydrazides, urea-amine hybrid curing systems, free radical initiators (e.g., peroxy esters, peroxy carbonates, hydroperoxides, alkylperoxides, arylperoxides, azo compounds, and the like), organic bases, transition metal catalysts, phenols, acid anhydrides, Lewis acids, Lewis bases, and the like.

When epoxy cure agents are present, invention compositions comprise in the range of about 0.1-2 wt % thereof. In certain embodiments, invention compositions comprise in the range of about 0.5-5 wt % of epoxy cure agent.

Maleimides, nadimides or itaconimides contemplated for use herein are compounds having the structure:

respectively, wherein:
m is 1-15,
p is 0-15,
each R$^2$ is independently selected from hydrogen or lower alkyl (such as C$_{1-5}$), and
J is a monovalent or a polyvalent radical comprising organic or organosiloxane radicals, and combinations of two or more thereof.

In some embodiments of the present invention, J is a monovalent or polyvalent radical selected from:
hydrocarbyl or substituted hydrocarbyl species typically having in the range of about 6 up to about 500 carbon atoms, where the hydrocarbyl species is selected from alkyl, alkenyl, alkynyl, cycloalkyl, cycloalkenyl, aryl, alkylaryl, arylalkyl, aryalkenyl, alkenylaryl, arylalkynyl or alkynylaryl, provided, however, that X can be aryl only when X comprises a combination of two or more different species;
hydrocarbylene or substituted hydrocarbylene species typically having in the range of about 6 up to about 500 carbon atoms, where the hydrocarbylene species are selected from alkylene, alkenylene, alkynylene, cycloalkylene, cycloalkenylene, arylene, alkylarylene, arylalkylene, arylalkenylene, alkenylarylene, arylalkynylene or alkynylarylene, heterocyclic or substituted heterocyclic species typically having in the range of about 6 up to about 500 carbon atoms, polysiloxane, or polysiloxane-polyurethane block copolymers, as well as combinations of one or more of the above with a linker selected from covalent bond, —O—, —S—, —NR—, —NR—C(O)—, —NR—C(O)—O—, —NR—C(O)—NR—, —S—C(O)—, —S—C(O)—O—, —S—C(O)—NR—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, or —NR—P(O)R$_2$—; where each R is independently hydrogen, alkyl or substituted alkyl.

Exemplary compositions include those wherein J is oxyalkyl, thioalkyl, aminoalkyl, carboxylalkyl, oxyalkenyl, thioalkenyl, aminoalkenyl, carboxyalkenyl, oxyalkynyl, thioalkynyl, aminoalkynyl, carboxyalkynyl, oxycycloalkyl, thiocycloalkyl, aminocycloalkyl, carboxycycloalkyl, oxycloalkenyl, thiocycloalkenyl, aminocycloalkenyl, carboxycycloalkenyl, heterocyclic, oxyheterocyclic, thioheterocyclic, aminoheterocyclic, carboxyheterocyclic, oxyaryl, thioaryl, aminoaryl, carboxyaryl, heteroaryl, oxyheteroaryl, thioheteroaryl, aminoheteroaryl, carboxyheteroaryl, oxyalkylaryl, thioalkylaryl, aminoalkylaryl, carboxyalkylaryl, oxyarylalkyl, thioarylalkyl, aminoarylalkyl, carboxyarylalkyl, oxyarylalkenyl, thioarylalkenyl, aminoarylalkenyl, carboxyarylalkenyl, oxyalkenylaryl, thioalkenylaryl, aminoalkenylaryl, carboxyalkenylaryl, oxyalkynylaryl, thioalkynylaryl, aminoalkynylaryl, carboxyarylalkynyl, oxyalkynylaryl, thioalkynylaryl, aminoalkynylaryl or carboxyalkynylaryl, oxyalkylene, thioalkylene, aminoalkylene, carboxyalkylene, oxyalkenylene, thioalkenylene, aminoalkenylene, carboxyalkenylene, oxyalkynylene, thioalkynylene, aminoalkynylene, carboxyalkynylene, oxycycloalkylene, thiocycloalkylene, aminocycloalkylene, carboxycycloalkylene, oxycycloalkenylene, thiocycloalkenylene, aminocycloalkenylene, carboxycycloalkenylene, oxyarylene, thioarylene, aminoarylene, carboxyarylene, oxyalkylarylene, thioalkylarylene, aminoalkylarylene, carboxyalkylarylene, oxyarylalkylene, thioarylalkylene, aminoarylalkylene, carboxyarylalkylene, oxyarylalkenylene, thioarylalkenylene, aminoarylalkenylene, carboxyarylalkenylene, oxyalkenylarylene, thioalkenylarylene, aminoalkenylarylene, carboxyalkenylarylene, oxyarylalkynylene, thioarylalkynylene, aminoarylalkynylene, carboxyarylalkynylene, oxyalkynylarylene, thioalkynylarylene, aminoalkynylarylene, carboxyalkynylarylene, heteroarylene, oxyheteroarylene, thioheteroarylene, aminoheteroarylene, carboxyheteroarylene, heteroatom-containing di- or polyvalent cyclic moiety, oxyheteroatom-containing di- or polyvalent cyclic moiety, thioheteroatom-containing di- or polyvalent cyclic moiety, aminoheteroatom-containing di- or polyvalent cyclic moiety, or a carboxyheteroatom-containing di- or polyvalent cyclic moiety.

Acrylates contemplated for use in the practice of the present invention are well known in the art. See, for example, U.S. Pat. No. 5,717,034, the entire contents of which are hereby incorporated by reference herein.

Exemplary acrylates contemplated for use herein include monofunctional (meth)acrylates, difunctional (meth)acrylates, trifunctional (meth)acrylates, polyfunctional (meth)acrylates, and the like.

Exemplary monofunctional (meth)acrylates include phenylphenol acrylate, methoxypolyethylene acrylate, acryloyloxyethyl succinate, fatty acid acrylate, methacryloyloxyethylphthalic acid, phenoxyethylene glycol methacrylate, fatty acid methacrylate, β-carboxyethyl acrylate, isobornyl acrylate, isobutyl acrylate, t-butyl acrylate, hydroxyethyl acrylate, hydroxypropyl acrylate, dihydrocyclopentadiethyl acrylate, cyclohexyl methacrylate, t-butyl methacrylate, dimethylaminoethyl methacrylate, diethylaminoethyl methacrylate, t-butylaminoethyl methacrylate, 4-hydroxybutyl acrylate, tetrahydrofurfuryl acrylate, benzyl acrylate, ethylcarbitol acrylate, phenoxyethyl acrylate, methoxytriethylene glycol acrylate, monopentaerythritol acrylate, dipentaerythritol acrylate, tripentaerythritol acrylate, polypentaerythritol acrylate, and the like.

Exemplary difunctional (meth)acrylates include hexanediol dimethacrylate, hydroxyacryloyloxypropyl methacrylate, hexanediol diacrylate, urethane acrylate, epoxyacrylate, bisphenol A-type epoxyacrylate, modified epoxyacrylate, fatty acid-modified epoxyacrylate, amine-modified bisphenol A-type epoxyacrylate, allyl methacrylate, ethylene glycol dimethacrylate, diethylene glycol dimethacrylate, ethoxylated bisphenol A dimethacrylate, tricyclodecanedimethanol dimethacrylate, glycerin dimethacrylate, polypropylene glycol diacrylate, propoxylated ethoxylated bisphenol A diacrylate, 9,9-bis(4-(2-acryloyloxyethoxy)phenyl)fluorene, tricyclodecane diacrylate, dipropylene glycol diacrylate, polypropylene glycol diacrylate, PO-modified neopentyl glycol diacrylate, tricyclodecanedimethanol diacrylate, 1,12-dodecanediol dimethacrylate, and the like.

Exemplary trifunctional (meth)acrylates include trimethylolpropane trimethacrylate, trimethylolpropane triacrylate, trimethylolpropane ethoxy triacrylate, polyether triacrylate, glycerin propoxy triacrylate, and the like.

Exemplary polyfunctional (meth)acrylates include dipentaerythritol polyacrylate, dipentaerythritol hexaacrylate, pentaerythritol tetraacrylate, pentaerythritolethoxy tetraacrylate, ditrimethylolpropane tetraacrylate, and the like.

Additional exemplary acrylates contemplated for use in the practice of the present invention include those described in U.S. Pat. No. 5,717,034, the entire contents of which are hereby incorporated by reference herein.

Optionally, one or more additional monomers or resins derived therefrom may be present in invention formulations, such as, for example, cyanate esters, silicones, oxetanes, polyesters, polyurethanes, polyimides, melamines, urea-formaldehydes, phenol-formaldehydes, and the like. When present, such materials may be present in the range of about 0.1 up to about 60 wt % based on the total weight of the final formulation.

When present, cyanate ester monomers contemplated for use in the practice of the present invention contain two or more ring forming cyanate (—O—C≡N) groups which cyclotrimerize to form substituted triazine rings upon heating. Because no leaving groups or volatile byproducts are formed during curing of the cyanate ester monomer, the curing reaction is referred to as addition polymerization. Suitable polycyanate ester monomers that may be used in the practice of the present invention include, for example, 1,1-bis(4-cyanatophenyl)methane, 1,1-bis(4-cyanatophenyl) ethane, 2,2-bis(4-cyanatophenyl)propane, bis(4-cyanatophenyl)-2,2-butane, 1,3-bis[2-(4-cyanato phenyl)propyl] benzene, bis(4-cyanatophenyl)ether, 4,4'-dicyanatodiphenyl, bis(4-cyanato-3,5-dimethylphenyl) methane, tris(4-cyanatophenyl)ethane, cyanated novolak, 1,3-bis[4-cyanatophenyl-1-(1-methylethylidene)]benzene, cyanated phenoldicyclopentadiene adduct, and the like. Polycyanate ester monomers utilized in accordance with the present invention may be readily prepared by reacting appropriate dihydric or polyhydric phenols with a cyanogen halide in the presence of an acid acceptor.

Monomers that can optionally be combined with polycyanate ester monomer(s) in accordance with the present invention are selected from those monomers which undergo addition polymerization. Such monomers include vinyl ethers, divinyl ethers, diallyl ethers, dimethacrylates, dipropargyl ethers, mixed propargyl allyl ethers, monomaleimides, bismaleimides, and the like. Examples of such monomers include cyclohexanedimethanol monovinyl ether, trisallylcyanurate, 1,1-bis(4-allyloxyphenyl)ethane, 1,1-bis (4-propargyloxyphenyl)ethane, 1,1-bis(4-allyloxyphenyl-4'-propargyloxyphenyl)ethane, dimethyltrimethylene acetal)-1-maleimidobenzene, 2,2,4-trimethylhexamethylene-1,6-bismaleimide, 2,2-bis[4-(4-maleimidophenoxy)phenyl] propane, and the like.

Additional cyanate esters contemplated for use in the practice of the present invention are well known in the art. See, for example, U.S. Pat. No. 5,718,941, the entire contents of which are hereby incorporated by reference herein.

When present, silicones contemplated for use in the practice of the present invention are well known in the art. See, for example, U.S. Pat. No. 5,717,034, the entire contents of which are hereby incorporated by reference herein.

When present, oxetanes (i.e., 1,3-propylene oxides) are heterocyclic organic compounds with the molecular formula $C_3H_6O$, having a four-membered ring with three carbon atoms and one oxygen atom. The term oxetane also refers generally to any organic compound containing an oxetane ring. See, for example, Burkhard et al., in Angew. Chem. Int. Ed. 2010, 49, 9052-9067, the entire contents of which are hereby incorporated by reference herein.

When present, polyesters contemplated for use in the practice of the present invention refer to condensation polymers formed by the reaction of polyols (also known as polyhydric alcohols), with saturated or unsaturated dibasic acids. Typical polyols used are glycols such as ethylene glycol; acids commonly used are phthalic acid and maleic acid. Water, a by-product of esterification reactions, is continuously removed, driving the reaction to completion. The use of unsaturated polyesters and additives such as styrene lowers the viscosity of the resin. The initially liquid resin is converted to a solid by cross-linking chains. This is done by creating free radicals at unsaturated bonds, which propagate to other unsaturated bonds in adjacent molecules in a chain reaction, linking the adjacent chains in the process.

When present, polyurethanes contemplated for use in the practice of the present invention refer to polymers composed of a chain of organic units joined by carbamate (urethane) links. Polyurethane polymers are formed by reacting an isocyanate with a polyol. Both the isocyanates and polyols used to make polyurethanes contain on average two or more functional groups per molecule.

When present, polyimides contemplated for use in the practice of the present invention refer to polymers composed of a chain of organic units joined by imide linkages (i.e., —C(O)—N(R)—C(O)—). Polyimide polymers can be formed by a variety of reactions, i.e., by reacting a dianhydride and a diamine, by the reaction between a dianhydride and a diisocyanate, and the like.

When present, melamines contemplated for use in the practice of the present invention refer to hard, thermosetting plastic materials made from melamine (i.e., 1,3,5-triazine-2,4,6-triamine) and formaldehyde by polymerization. In its butylated form, it can be dissolved in n-butanol and/or xylene. It can be used to cross-link with other resins such as alkyd, epoxy, acrylic, and polyester resins.

When present, urea-formaldehydes contemplated for use in the practice of the present invention refers to a non-transparent thermosetting resin or plastic made from urea and formaldehyde heated in the presence of a mild base such as ammonia or pyridine.

When present, phenol-formaldehydes contemplated for use in the practice of the present invention refer to synthetic polymers obtained by the reaction of phenol or substituted phenol with formaldehyde.

Particulate fillers contemplated for use in the practice of the present invention include silica, calcium silicate, aluminum hydroxide, magnesium hydroxide, calcium carbonate, magnesium carbonate, aluminum oxide ($Al_2O_3$), zinc oxide (ZnO), magnesium oxide (MgO), aluminum nitride (AlN), boron nitride (BN), carbon nanotubes, diamond, clay, aluminosilicate, and the like, as well as mixtures of any two or more thereof. In some embodiments, the particulate filler is sililca.

Typically, fillers employed in invention formulations have a particle size in the range of about 0.005 μm (i.e., 5 nm) up to about 20 μm. In certain embodiments, filler employed herein has a particle size in the range of about 0.1 μm up to about 5 μm.

Compositions according to the present invention comprise in the range of about 30-75 wt % of said particulate filler. In some embodiments, compositions according to the present invention comprise in the range of about 40-60 wt % of said particulate filler.

Invention compositions typically comprise:
at least 1 wt % of said epoxy resin,
at least 6 wt % of said maleimide, nadimide or itaconimide,
at least 4 wt % of said acrylate, and
at least 30 wt % of said filler.

In some embodiments, invention compositions may further comprise one or more of:
at least 1 wt % of a fluxing agent,
at least 0.1 wt % of an adhesion promoter; and/or
at least 4 wt % of a toughening agent.

In some embodiments, invention compositions may further comprise one or more of:
up to about 10 wt % of a fluxing agent,
up to about 2 wt % of an adhesion promoter; and/or
up to about 16 wt % of a toughening agent.

In some embodiments, invention compositions comprise:
in the range of about 1 up to 20 wt % of said epoxy resin,
in the range of about 6 up to 16 wt % of said maleimide, nadimide or itaconimide,
in the range of about 4 up to 12 wt % of said acrylate, and
in the range of about 30 up to 75 wt % of said filler.

Such compositions may further comprise one or more of:
at least 1, up to about 10 wt % of a fluxing agent,
at least 0.1, up to about 2 wt % of an adhesion promoter; and/or
at least 4, up to about 16 wt % of a toughening agent.

Invention compositions may optionally further comprise in the range of about 0.2-2 wt % of a free-radical polymerization initiator. In certain embodiments, invention compositions may further comprise in the range of about 0.2-1 wt % of a free radical polymerization initiator.

Exemplary free radical initiators include peroxy esters, peroxy carbonates, hydroperoxides, alkylperoxides, arylperoxides, azo compounds, and the like.

Invention compositions optionally further comprise one or more flow additives, adhesion promoters, rheology modifiers, toughening agents, fluxing agents, film flexibilizers, an epoxy-curing catalyst (e.g., imidazole), a curing agent (e.g., a radical initiator such as dicumyl peroxide), radical polymerization regulator (e.g., 8-hydroxy quinoline), and/or radical stabilizer, as well as mixtures of any two or more thereof.

As used herein, the term "flow additives" refers to compounds which modify the viscosity of the formulation to which they are introduced. Exemplary compounds which impart such properties include silicon polymers, ethyl acrylate/2-ethylhexyl acrylate copolymers, alkylol ammonium salts of phosphoric acid esters of ketoxime, and the like, as well as combinations of any two or more thereof.

As used herein, the term "adhesion promoters" refers to compounds which enhance the adhesive properties of the formulation to which they are introduced.

As used herein, the term "rheology modifiers" refers to additives which modify one or more physical properties of the formulation to which they are introduced.

As used herein, the term "toughening agents" refers to additives which enhance the impact resistance of the formulation to which they are introduced.

As used herein, the term "fluxing agents" refers to reducing agents which prevent oxides from forming on the surface of the molten metal. The composition of claim 1 wherein said fluxing agent is a carboxylic acid, including rosin gum, dodecanedioic acid (commercially available as Corfree M2 from Aldrich), adipic acid, sebasic acid, polysebasic polynhydride, maleic acid, tartaric acid, citric acid, and the like. Fluxing agents may also include alcohols, hydroxyl acid and hydroxyl base. Exemplary fluxing materials include polyols (e.g., ethylene glycol, glycerol, 3-[bis(glycidyl oxy methyl) methoxy]-1,2-propane diol, D-ribose, D-cellobiose, cellulose, 3-cyclohexene-1,1-dimethanol and the like.

As used herein, the term "radical stabilizers" refers to compounds such as hydroquinones, benzoquinones, hindered phenols, hindered amines (e.g., thiocarbonylthio-based compounds), benzotriazole-based ultraviolet absorbers, triazine-based ultraviolet absorbers, benzophenone-based ultraviolet absorbers, benzoate-based ultraviolet absorbers, hindered amine-based ultraviolet absorbers, nitroxide radical-based compounds, and the like, as well as combinations of any two or more thereof.

When present, invention compositions comprise in the range of about 0.1-1 wt % of said radical stabilizer. In some embodiments, invention compositions comprise in the range of about 0.1-0.6 wt % of said radical stabilizer.

Invention compositions may also optionally contain one or more diluents. When diluent is present, invention compositions comprise in the range of about 10-50 wt % diluent, relative to the total composition. In certain embodiments, invention compositions comprise in the range of about 20-40 wt % diluent.

Exemplary diluents contemplated for use herein, when present, include aromatic hydrocarbons (e.g., benzene, toluene, xylene, and the like), saturated hydrocarbons (e.g., hexane, cyclohexane, heptane, tetradecane), chlorinated hydrocarbons (e.g., methylene chloride, chloroform, carbon tetrachloride, dichloroethane, trichloroethylene, and the like), ethers (e.g., diethyl ether, tetrahydrofuran, dioxane, glycol ethers, monoalkyl or dialkyl ethers of ethylene glycol, and the like), polyols (e.g., polyethylene glycol, propylene glycol, polypropylene glycol, and the like), esters (e.g., ethyl acetate, butyl acetate, methoxy propyl acetate, and the like); dibasic esters, alpha-terpineol, beta-terpineol, kerosene, dibutylphthalate, butyl carbitol, butyl carbitol acetate, carbitol acetate, ethyl carbitol acetate, hexylene glycol, high boiling alcohols and esters thereof, glycol ethers, ketones (e.g., acetone, methyl ethyl ketone, and the like), amides (e.g., dimethylformamide, dimethylacetamide, and the like), heteroaromatic compounds (e.g., N-methylpyrrolidone, and the like), and the like, as well as mixtures of any two or more thereof.

Hydroxy-containing diluents contemplated for use herein include water and hydroxy-containing compounds having a $C_1$ up to about a $C_{10}$ backbone. Exemplary hydroxy-containing diluents include water, methanol, ethanol, propanol, ethylene glycol, propylene glycol, glycerol, terpineol, and the like, as well as mixtures of any two or more thereof.

The amount of hydroxy-containing diluent contemplated for use in accordance with the present invention can vary widely, typically falling in the range of about 5 up to about 80 weight percent of the composition. In certain embodiments, the amount of hydroxy-containing diluent falls in the range of about 10 up to 60 weight percent of the total composition. In some embodiments, the amount of hydroxy-containing diluent falls in the range of about 20 up to about 50 weight percent of the total composition.

Optionally, compositions described herein may include flow additives, and the like. Flow additives contemplated for optional use herein include silicon polymers, ethyl acrylate/2-ethylhexyl acrylate copolymers, alkylol ammonium salt of phosphoric acid esters of ketoxime, and the like, as well as combinations of any two or more thereof.

In accordance with another embodiment of the present invention, there are provided underfill films comprising the reaction product of curing compositions according to the present invention.

Underfill films according to the invention typically absorb less than 2% by weight moisture when exposed to 85° C. at 85% relative humidity for about 2 days; in some embodiments, underfillfilms according to the invention typically absorb less than 1.5% by weight moisture when exposed to 85° C. at 85% relative humidity for about 2 days; in some embodiments, underfill films according to the invention typically absorb less than 1.2% by weight moisture when exposed to 85° C. at 85% relative humidity for about 2 days; in some embodiments, underfill films according to the invention typically absorb less than 1.0% by weight moisture when exposed to 85° C. at 85% relative humidity for about 2 days.

Underfill films according to the invention, when B-staged, after cure, have a Tg, as determined by thermomechanical analysis (TMA), of greater than about 80° C.

Underfill films according to the invention can be further characterized as having a die shear at 260° C. of at least 5 kg/cm$^2$ (as tested with SiN die/PI die/SiO$_2$ (size: 3.81×3.81× 700 mm$^3$), wherein the die is attached on a BT substrate at 120° C./1 kg force/5 seconds, then cured by ramping the temperature from room temperature to 175° C. over 30 minutes, then held at 175° C. for 5 hrs.

In accordance with another embodiment of the present invention, there are provided methods for preparing underfill films, said methods comprising curing a composition as described herein after application thereof to a suitable substrate.

In accordance with yet another embodiment of the present invention, there are provided articles comprising an underfill film as described herein adhered to a suitable substrate therefor.

Suitable substrates contemplated for use herein include polyethylene terephthalates, polymethyl methacrylates, polyethylenes, polypropylenes, polycarbonates, epoxy resins, polyimides, polyamides, polyesters, glass, Si die with silicon nitride passivation, Si die with polyimide passivation, BT substrates, bare Si, SR4 substrates, SR5 substrates, and the like.

The adhesion of said underfill film to said substrate in invention articles is typically at least 5 kg/cm$^2$ as tested with SiN die/PI die/SiO$_2$ (size: 3.81×3.81×700 mm$^3$), wherein the die is attached on a BT substrate at 120° C./1 kg force/5 seconds, then cured by ramping the temperature from room temperature to 175° C. over 30 minutes, then held at 175° C. for 5 hrs.

A variety of articles can be prepared employing invention materials, including, for example, flip chip packages, stacked die, hybrid memory cubes, TSV devices, and the like.

Various aspects of the present invention are illustrated by the following non-limiting examples. The examples are for illustrative purposes and are not a limitation on any practice of the present invention. It will be understood that variations and modifications can be made without departing from the spirit and scope of the invention. One of ordinary skill in the art readily knows how to synthesize or commercially obtain the reagents and components described herein.

EXAMPLES

In accordance with one aspect of the present invention, there are provided methods for preparing compositions according to the present invention. In one embodiment of the present invention, the method includes a first step of dispersing the filler into the liquids using approaches like 3-roll milling, ball milling, etc. The purpose is to break down any agglomerations of particles into individual sub-micron particles. The subsequent step is to add any other raw materials contemplated for use and subjecting the resulting combination to shear mixing sufficient to prepare a varnish for film coating. Exemplary formulations which fall within the scope of the present claims are presented in Table 1.

TABLE 1

| | Formulation 1 | Formulation 2 | Formulation 3 |
|---|---|---|---|
| Mixture of epoxy resins[1] | 12.0 | 8 | 2.01 |
| Mixture of acrylate resins[2] | 15.0 | 10.0 | 12.8 |
| Mixture of BMI resins[3] | 15.1 | 10.1 | 11.06 |
| Adhesion promoter (silane coupling agent, etc.) | 1.5 | 1.0 | 1..08 |
| Epoxy hardener (imidazole based curing agent, phenol novolac hardener, etc.) | 0.2 | 0.13 | 0.2 |
| Radical initiator[4] | 0.6 | 0.4 | 0.5 |

TABLE 1-continued

| | Formulation 1 | Formulation 2 | Formulation 3 |
|---|---|---|---|
| Silica fillers (average <1 um) | | 60 | 60.18 |
| Silica fillers (average <0.1 um) | 40 | | |
| Additives (toughening agent, etc.) | 15.6 | 10.4 | 12.17 |
| Total | 100 | 100 | 100 |

[1]Exemplary combinations include Epiclon 850CRP and siloxane-modified epoxy resins
[2]Exemplary resins include SEA-187 epoxy acrylate
[3]Exemplary resins include BMI-1700 amorphous rein
[4]Exemplary initiators include Perkadox 14S, Luperox 101, dicumyl peroxide, and Trigonox 145-E85

Each of the formulations described above were subjected to performance tests (for which the results are set forth in the following Table 2).

TABLE 2

| | Formulation 1 | Formulation 2 | Formulation 3 |
|---|---|---|---|
| DSC onset temperature (° C.) | 163 | 161 | 173 |
| DSC peak temperature (° C.) | 168 | 169 | 189 |
| DeltaT between onset and peak temperature (° C.) | 5 | 8 | 16 |

Differential scanning calorimetry (DCS) data in Table 2 shows that all formulations have fast curing properties, with the deltaT between "DSC onset" and "DSC peak" temperatures being less than 20° C.; in some embodiments, the deltaT is less than 15° C.; and in some embodiments, the deltaT is less than 10 deg C.

The results set forth above demonstrate that with a unique hybrid resin system such as the resin systems described herein, fast cure type underfill film materials can be achieved.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

That which is claimed is:

1. A composition comprising:
   an epoxy resin;
   a maleimide, nadimide or itaconimide;
   an acrylate; and
   a filler;
   wherein:
   said epoxy resin is a thermosetting resin which can cure into a three-dimensional polymer network;
   said maleimide, nadimide or itaconimide is monomeric or oligomeric and can undergo radical cure to form a polymeric network;

said acrylate is monomeric or oligomeric and can undergo radical cure to form a polymeric network; and said filler modulates the coefficient of thermal expansion (CTE) of the resulting composition;

wherein:

said composition, when cured, has a:

DSC onset of 100° C. 205° C.;

Melt viscosity in the range of 200 Poise-40,000 Poise, and gelling temperature of 130° C. 180° C., as measured by Ares Rheometer at 10 Rad frequency with a 10° C./min ramp rate using a sample 1 inch in diameter and 1 mm thick.

2. The composition of claim 1 wherein said epoxy resin comprises a polymeric backbone having one or more epoxide groups thereon.

3. The composition of claim 2 wherein said epoxy resin is selected from bisphenol A epoxy resins, bisphenol F epoxy resins, naphthalene epoxy resins, novolac epoxy resins, siloxane-modified epoxy resins, cycloaliphatic epoxy resins, biphenyl epoxy resins, DCPD epoxy resins, or modified epoxy resins, as well as combinations of any two or more thereof.

4. The composition of claim 3 wherein said siloxane modified epoxy resin has the structure:

wherein:

Z is —O—(CH$_2$)$_3$—O-Ph-CH$_2$-Ph-O—(CH$_2$—CH(OH)—CH$_2$—O-Ph-CH$_2$-Ph-O—)$_n$—CH$_2$-oxirane, and n falls in the range of about 1-4.

5. The composition of claim 4 wherein said siloxane modified epoxy resin is produced by contacting a combination of the following components under conditions suitable to promote the reaction thereof

+

+ wherein "n" falls in the range of about 1-4.

6. The composition of claim 1 wherein said maleimide, nadimide or itaconimide, has the structure:

respectively, wherein:

m is 1-15, p is 0-15, each $R^2$ is independently selected from hydrogen or lower alkyl (such as $C_{1-5}$), and J is a monovalent or a polyvalent radical comprising organic or organosiloxane radicals, and combinations of two or more thereof.

7. The composition of claim 6 wherein J is a monovalent or polyvalent radical selected from:

hydrocarbyl or substituted hydrocarbyl species typically having in the range of about 6 up to about 500 carbon atoms, where the hydrocarbyl species is selected from alkyl, alkenyl, alkynyl, cycloalkyl, cycloalkenyl, aryl, alkylaryl, arylalkyl, aryalkenyl, alkenylaryl, arylalkynyl or alkynylaryl, provided, however, that X can be aryl only when X comprises a combination of two or more different species;

hydrocarbylene or substituted hydrocarbylene species typically having in the range of about 6 up to about 500 carbon atoms, where the hydrocarbylene species are selected from alkylene, alkenylene, alkynylene, cycloalkylene, cycloalkenylene, arylene, alkylarylene, arylalkylene, arylalkenylene, alkenylarylene, arylalkynylene or alkynylarylene, heterocyclic or substituted heterocyclic species typically having in the range of about 6 up to about 500 carbon atoms, polysiloxane, or polysiloxane-polyurethane block copolymers, as well as combinations of one or more of the above with a linker selected from covalent bond, —O—, —S—, —NR—, —NR—C(O)—, —NR—C(O)—O—, —NR—C(O)—NR—, —S—C(O)—, —S—C(O)—O—, —S—C(O)—NR—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, S(O)$_2$—O—, —O—NR—S(O)$_2$—NR—, —O—NR—S(O)$_2$—, —O—P(O)R$_2$—, —S—P(O)R$_2$—, or —NR—P(O)R$_2$—;

where each R is independently hydrogen, alkyl or substituted alkyl.

8. The composition of claim 6 wherein J is oxyalkyl, thioalkyl, aminoalkyl, carboxylalkyl, oxyalkenyl, thioalkenyl, aminoalkenyl, carboxyalkenyl, oxyalkynyl, thioalkynyl, aminoalkynyl, carboxyalkynyl, oxycycloalkyl, thiocycloalkyl, aminocycloalkyl, carboxycycloalkyl, oxycloalkenyl, thiocycloalkenyl, aminocycloalkenyl, carboxycycloalkenyl, heterocyclic, oxyheterocyclic, thioheterocyclic, aminoheterocyclic, carboxyheterocyclic, oxyaryl, thioaryl, aminoaryl, carboxyaryl, heteroaryl, oxyheteroaryl, thioheteroaryl, aminoheteroaryl, carboxyheteroaryl, oxyalkylaryl, thioalkylaryl, aminoalkylaryl, carboxyalkylaryl, oxyarylalkyl, thioarylalkyl, aminoarylalkyl, carboxyarylalkyl, oxyarylalkenyl, thioarylalkenyl, aminoarylalkenyl, carboxyarylalkenyl, oxyalkenylaryl, thioalkenylaryl, aminoalkenylaryl, carboxyalkenylaryl, oxyarylalkynyl, thioarylalkynyl, aminoarylalkynyl, carboxyarylalkynyl, oxyalkynylaryl, thioalkynylaryl, aminoalkynylaryl or carboxyalkynylaryl, oxyalkylene, thioalkylene, aminoalkylene, carboxyalkylene, oxyalkenylene, thioalkenylene, aminoalkenylene, carboxyalkenylene, oxyalkynylene, thioalkynylene, aminoalkynylene, carboxyalkynylene, oxycycloalkylene, thiocycloalkylene, aminocycloalkylene, carboxycycloalkylene, oxycycloalkenylene, thiocycloalkenylene, aminocycloalkenylene, carboxycycloalkenylene, oxyarylene, thioarylene, aminoarylene, carboxyarylene, oxyalkylarylene, thioalkylarylene, aminoalkylarylene, carboxyalkylarylene, oxyarylalkylene, thioarylalkylene, aminoarylalkylene, carboxyarylalkylene, oxyarylalkenylene, thioarylalkenylene, aminoarylalkenylene, carboxyarylalkenylene, oxyalkenylarylene, thioalkenylarylene, aminoalkenylarylene, carboxyalkenylarylene, oxyarylalkynylene, thioarylalkynylene, aminoarylalkynylene, carboxyarylalkynylene, oxyalkynylarylene, thioalkynylarylene, aminoalkynylarylene, carboxyalkynylarylene, heteroarylene, oxyheteroarylene, thioheteroarylene, aminoheteroarylene, carboxyheteroarylene, heteroatom-containing di- or polyvalent cyclic moiety, oxyheteroatom-containing di- or polyvalent cyclic moiety, thioheteroatom-containing di- or polyvalent cyclic moiety, aminoheteroatom-containing di- or polyvalent cyclic moiety, or a carboxyheteroatom-containing di- or polyvalent cyclic moiety.

9. The composition of claim 1 further comprising an organic diluent.

10. The composition of claim 1 wherein said composition comprises:
at least 1 wt % of said epoxy resin,
at least 6 wt % of said maleimide, nadimide or itaconimide,
at least 4 wt % of said acrylate, and
at least 30 wt % of said filler.

11. The composition of claim 10, further comprising one or more of:
at least 1 wt % of a fluxing agent,
at least 0.1 wt % of an adhesion promoter; and/or
at least 4 wt % of a toughening agent.

12. The composition of claim 1 wherein said composition comprises:
in the range of about 1 up to 20 wt % of said epoxy resin,
in the range of about 6 up to 16 wt % of said maleimide, nadimide or itaconimide,
in the range of about 4 up to 12 wt % of said acrylate, and
in the range of about 30 up to 75 wt % of said filler.

13. The composition of claim 12, further comprising one or more of:
at least 1 wt % of a fluxing agent,
at least 0.1 wt % of an adhesion promoter; and/or
at least 4 wt % of a toughening agent.

14. An underfill film comprising the reaction product of curing the composition of claim 1.

15. The underfill film of claim 14 wherein said film absorbs less than 2% by weight moisture when exposed to 85° C. at 85% relative humidity for about 2 days.

16. The underfill film of claim 14 wherein the film is a B-staged film, which, after cure, has a Tg, as determined by thermomechanical analysis (TMA), of greater than about 80° C.

17. The underfill film of claim 14 wherein the die shear of said film at 260° C. is at least 5 kg/cm$^2$ as tested with SiN die/PI die/SiO$_2$ (size: 3.81×3.81×700 mm$^3$), wherein the die is attached on a BT substrate at 120° C./1 kg force/5 seconds, then cured by ramping the temperature from room temperature to 175° C. over 30 minutes, then held at 175° C. for 5 hrs.

18. A method for preparing an underfill film, said method comprising curing the composition of claim 1 after application thereof to a suitable substrate.

19. An article comprising an underfill film according to claim 14 adhered to a suitable substrate therefor, wherein said suitable substrate is a polyethylene terephthalate, a polymethyl methacrylate, a polyethylene, a polypropylene, a polycarbonate, an epoxy resin, a polyimide, a polyamide, a polyester, glass, a Si die with silicon nitride passivation, a Si die with polyimide passivation, a BT substrate, bare Si, a SR4 substrate, or a SR5 substrate.

20. The article of claim 19 wherein said article is a flip chip package, a stacked die, a hybrid memory cube, or a TSV device.

21. The article of claim 19 wherein the adhesion of said underfill film to said substrate is at least 5 kg/cm$^2$ as tested with SiN die/PI die/SiO$_2$ (size: 3.81×3.81×700 mm$^3$), wherein the die is attached on a BT substrate at 120° C./1 kg force/5 seconds, then cured by ramping the temperature from room temperature to 175° C. over 30 minutes, then held at 175° C. for 5 hrs.

* * * * *

UNITED STATES PATENT AND TRADEMARK OFFICE
CERTIFICATE OF CORRECTION

PATENT NO. : 10,242,923 B2
APPLICATION NO. : 15/945772
DATED : March 26, 2019
INVENTOR(S) : Jie Bai et al.

Page 1 of 1

It is certified that error appears in the above-identified patent and that said Letters Patent is hereby corrected as shown below:

In the Specification

Column 4, Line 43: Change "14" to "1-4".

Column 9, Line 28: Change "dimethyltrimethylene acetal)-1-maleimidobenzene" to "3-(2,2-dimethyltrimethylene acetal)-1-maleimidobenzene".

Signed and Sealed this
Tenth Day of December, 2019

Andrei Iancu
*Director of the United States Patent and Trademark Office*